United States Patent
Nagura et al.

(10) Patent No.: US 9,986,953 B2
(45) Date of Patent: Jun. 5, 2018

(54) PRODUCTION METHOD FOR RADIATION DETECTION UNIT

(71) Applicant: HAMAMATSU PHOTONICS K.K., Hamamatsu-shi, Shizuoka (JP)

(72) Inventors: Keisuke Nagura, Hamamatsu (JP); Kento Matsushima, Hamamatsu (JP); Mitsutoshi Sugiya, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 289 days.

(21) Appl. No.: 14/898,241

(22) PCT Filed: Mar. 31, 2014

(86) PCT No.: PCT/JP2014/059439
§ 371 (c)(1),
(2) Date: Dec. 14, 2015

(87) PCT Pub. No.: WO2014/203588
PCT Pub. Date: Dec. 24, 2014

(65) Prior Publication Data
US 2016/0128652 A1    May 12, 2016

(30) Foreign Application Priority Data
Jun. 18, 2013   (JP) ................. 2013-127550

(51) Int. Cl.
*A61B 6/03* (2006.01)
*A61B 6/00* (2006.01)

(52) U.S. Cl.
CPC .............. *A61B 6/035* (2013.01); *A61B 6/032* (2013.01); *A61B 6/42* (2013.01); *A61B 6/4233* (2013.01); *A61B 6/4266* (2013.01)

(58) Field of Classification Search
CPC ......... A61B 6/035; A61B 6/4266; A61B 6/42; A61B 6/032; A61B 6/4233
See application file for complete search history.

(56) References Cited

U.S. PATENT DOCUMENTS

| 4,338,521 A | 7/1982 | Shaw et al. |
| 2006/0110956 A1* | 5/2006 | Lacey ............... A61B 6/032 439/108 |

(Continued)

FOREIGN PATENT DOCUMENTS

| CN | 1139872 | 1/1997 |
| CN | 101523892 | 9/2009 |

(Continued)

OTHER PUBLICATIONS

International Preliminary Report on Patentability dated Dec. 30, 2015 for PCT/JP2014/059439.

*Primary Examiner* — John C Hong
(74) *Attorney, Agent, or Firm* — Drinker Biddle & Reath LLP

(57) ABSTRACT

According to a method for producing a radiation detection unit, in a first step, a side portion of a first radiation detection module and a first protrusion are abutted. In a second step, a second radiation detection module is arranged within a region from which the first protrusion has been removed, and a side portion of the second radiation detection module and a second protrusion are abutted, after the first step. In a third step, each of the mounting portion of the first radiation detection module and the mounting portion of the second radiation detection module is arranged opposing a frame while spaced apart from the frame, and each of the first radiation detection module and the second radiation detection module is mounted on the frame.

4 Claims, 12 Drawing Sheets

(56) References Cited

U.S. PATENT DOCUMENTS

| | | | |
|---|---|---|---|
| 2008/0230706 A1* | 9/2008 | Dorscheid | G01T 1/2018 250/363.05 |
| 2011/0113611 A1 | 5/2011 | Tonami et al. | |
| 2012/0049074 A1 | 3/2012 | Luhta et al. | |
| 2012/0069956 A1 | 3/2012 | Guery et al. | |
| 2012/0305782 A1 | 12/2012 | Burr et al. | |
| 2016/0128654 A1* | 5/2016 | Wollowick | A61B 6/12 600/424 |

FOREIGN PATENT DOCUMENTS

| | | |
|---|---|---|
| CN | 101806909 | 8/2010 |
| CN | 101806913 | 8/2010 |
| CN | 102428388 | 4/2012 |
| JP | S59-058379 | 4/1984 |
| JP | H01-126584 A | 5/1989 |
| JP | H09-508305 A | 8/1997 |
| JP | H9-508309 | 8/1997 |
| JP | 2013-064627 | 4/2013 |

\* cited by examiner

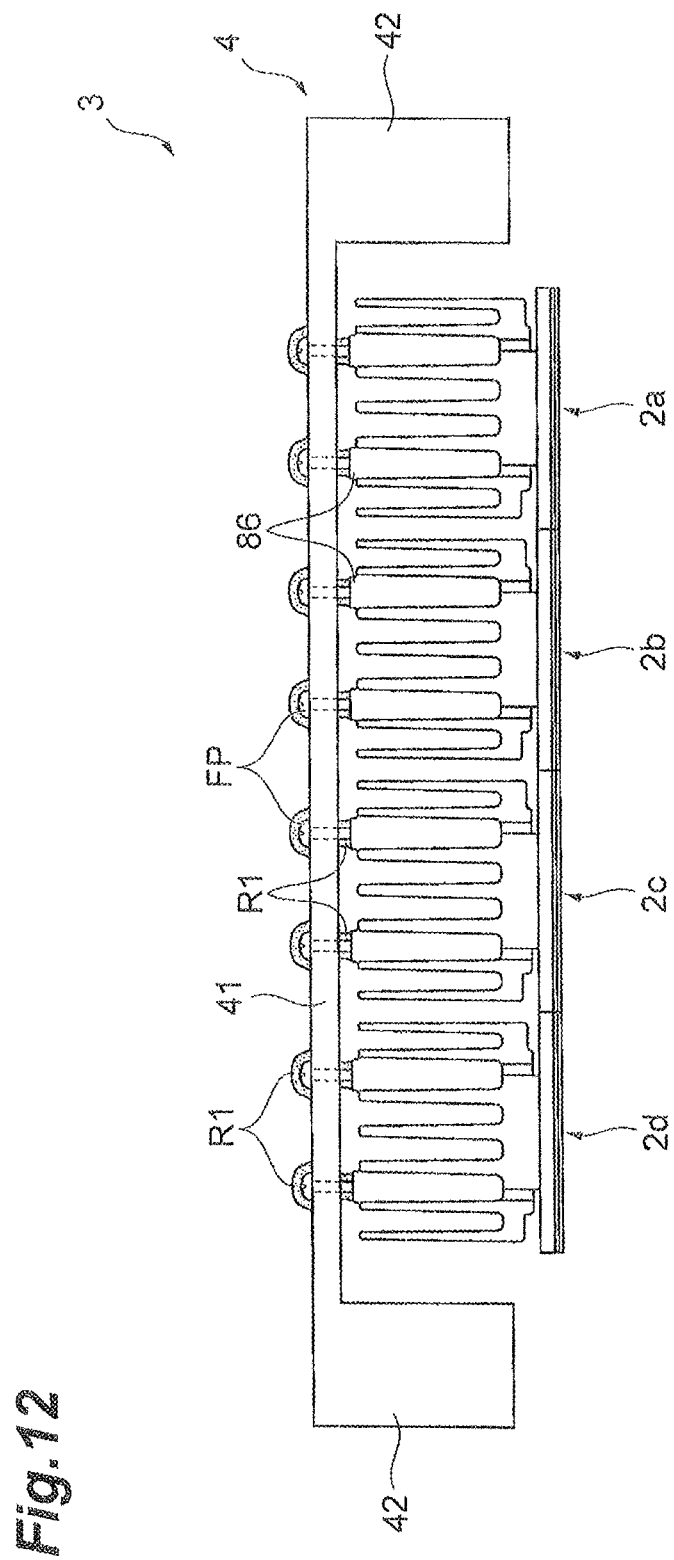

PRODUCTION METHOD FOR RADIATION DETECTION UNIT

TECHNICAL FIELD

The present invention relates to a method for producing a radiation detection unit for a computed tomography (CT) device.

BACKGROUND ART

Conventionally, a radiation detection unit equipped with a plurality of radiation detection modules for detecting radiation including X-ray is known (refer to Patent Literature 1, for example). Patent Literature 1 describes a detector assembly equipped with a plurality of detector modules. The detector assembly includes the plurality of detector modules described above and an arcuate supporting reference spine provided in a channel direction. The plurality of detector modules is mounted on the supporting reference spine in the channel direction.

CITATION LIST

Patent Literature

Patent Literature 1: Japanese Unexamined Patent Application Publication (Translation of PCT Application) No. 09-508305

SUMMARY OF INVENTION

Technical Problem

In the above-described radiation detection unit, it is desirable to improve positional accuracy of the radiation detection module to improve radiation detection accuracy. Furthermore, to increase resolution in the radiation detection unit, it is desirable to reduce a distance between the radiation detection modules.

The present invention is directed to solve the problems as described above. An object of the invention is to provide a method for producing a radiation detection unit capable of improving positional accuracy of the radiation detection module and reducing the distance between the radiation detection modules.

Solution to Problem

A method for producing a radiation detection unit according to an aspect of the present invention is a method for producing a radiation detection unit for a CT device. The radiation detection unit includes: a first radiation detection module and a second radiation detection module each module configured to detect radiation; and a frame configured to support each of the first radiation detection module and the second radiation detection module, wherein each of the first radiation detection module and the second radiation detection module includes an incident surface on which radiation is incident, a mounting portion located on an opposite side of the incident surface, and a side portion exposed in a direction orthogonal to a normal of the incident surface. The method for producing the radiation detection unit is implemented by using a jig including a reference surface, a first protrusion protruding from the reference surface and a second protrusion protruding from the reference surface, the first protrusion being removable from the jig. The method for producing the radiation detection unit includes: a first step of abutting the incident surface of the first radiation detection module and the reference surface of the jig so as to position the first radiation detection module; a second step of abutting the incident surface of the second radiation detection module and the reference surface of the jig so as to position the second radiation detection module; and a third step of mounting each of the first radiation detection module and the second radiation detection module on the frame. In the first step, the side portion of the first radiation detection module and the first protrusion are abutted. In the second step, the second radiation detection module is arranged within a region from which the first protrusion has been removed, and the side portion of the second radiation detection module and the second protrusion are abutted, after the first step. In the third step, each of the mounting portion of the first radiation detection module and the mounting portion of the second radiation detection module is arranged opposing the frame and spaced apart from the frame and each of the first radiation detection module and the second radiation detection module is mounted on the frame.

In the method for producing the radiation detection unit, each of the first radiation detection module and the second radiation detection module is positioned in each of separate steps. This enables suppressing accumulation of a dimensional error and an assembly error on the first radiation detection module and the second radiation detection module. Accordingly, this improves positional accuracy of the radiation detection module in an arrangement direction of the first radiation detection module and the second radiation detection module. Furthermore, the first protrusion for positioning the first radiation detection module is removable from the jig. In the second step, in positioning the second radiation detection module, the second radiation detection module is arranged in a region from which the first protrusion has been removed. This enables arranging the first radiation detection module and the second radiation detection module close to each other. Accordingly, this reduces the distance between the radiation detection modules. Furthermore, in the third step, while the incident surface of the first radiation detection module and the incident surface of the second radiation detection module being in states of abutting the reference surface that is common to the modules, each of the mounting portions of the radiation detection modules is mounted on the frame so as to be spaced apart from the frame. This makes it possible to align the incident surface of the first radiation detection module and the incident surface of the second radiation detection module, and simultaneously absorb the dimensional error and the assembly error of the radiation detection module, at a gap between the mounting portion of the radiation detection module and the frame. Accordingly, this improves positional accuracy of the radiation detection module in a normal direction of the incident surface. As described above, a method for producing the radiation detection unit according to an aspect of the present invention enables improving positional accuracy of the radiation detection module and reducing the distance between the radiation detection modules.

On each of the mounting portion of the first radiation detection module and the mounting portion of the second radiation detection module, a hole into which a rod member can be inserted may be provided. In the third step, adhesive may be filled in each of the hole of the first radiation detection module and the hole of the second radiation detection module, a rod member may be inserted into each of the holes, and each of the first radiation detection module and the second radiation detection module may be mounted on the frame via the rod member. In this case, each of the first radiation detection module and the second radiation detection module can be fixed with adhesive to the frame in higher accuracy and more firmly.

The jig may include: a reference jig having the reference surface and a back surface on the opposite side of the reference surface; a first protrusion jig having the first protrusion; and a second protrusion jig having the second protrusion. The reference jig may include a first through hole for the first protrusion to penetrate from the back surface to the reference surface, and a second through hole for the second protrusion to penetrate from the back surface to the reference surface. In the first step, the reference jig and the first protrusion jig may be combined for use such that the first protrusion protrudes from the reference surface. In the second step, the reference jig and the second protrusion jig may be combined for use such that the second protrusion protrudes from the reference surface after the first protrusion jig has been removed from the reference jig. In this case, in removing the first protrusion from the jig, it is only required to remove the first protrusion jig from the back surface of the reference jig. This facilitates removing the first protrusion from the jig. Accordingly, this improves assemblability of the radiation detection unit.

The frame may extend in a first direction along a slice direction of the CT device. The first radiation detection module and the second radiation detection module may be mounted on the frame along the first direction. In this case, it is possible to improve positional accuracy of the radiation detection module in the slice direction.

Advantageous Effects of Invention

According to the present invention, it is possible to provide a method for producing a radiation detection unit capable of improving positional accuracy of the radiation detection module and method for producing reducing the distance between the radiation detection modules.

BRIEF DESCRIPTION OF DRAWINGS

FIG. 12 is a front view of a step of the method for producing the radiation detection unit according to the embodiment.

DESCRIPTION OF EMBODIMENTS

Hereinafter, a method for producing a radiation detection unit according to an embodiment will be described with reference to the drawings. The same reference signs are given to same or similar components, and duplicate descriptions will be omitted.

[CT Device]

Figure 1:
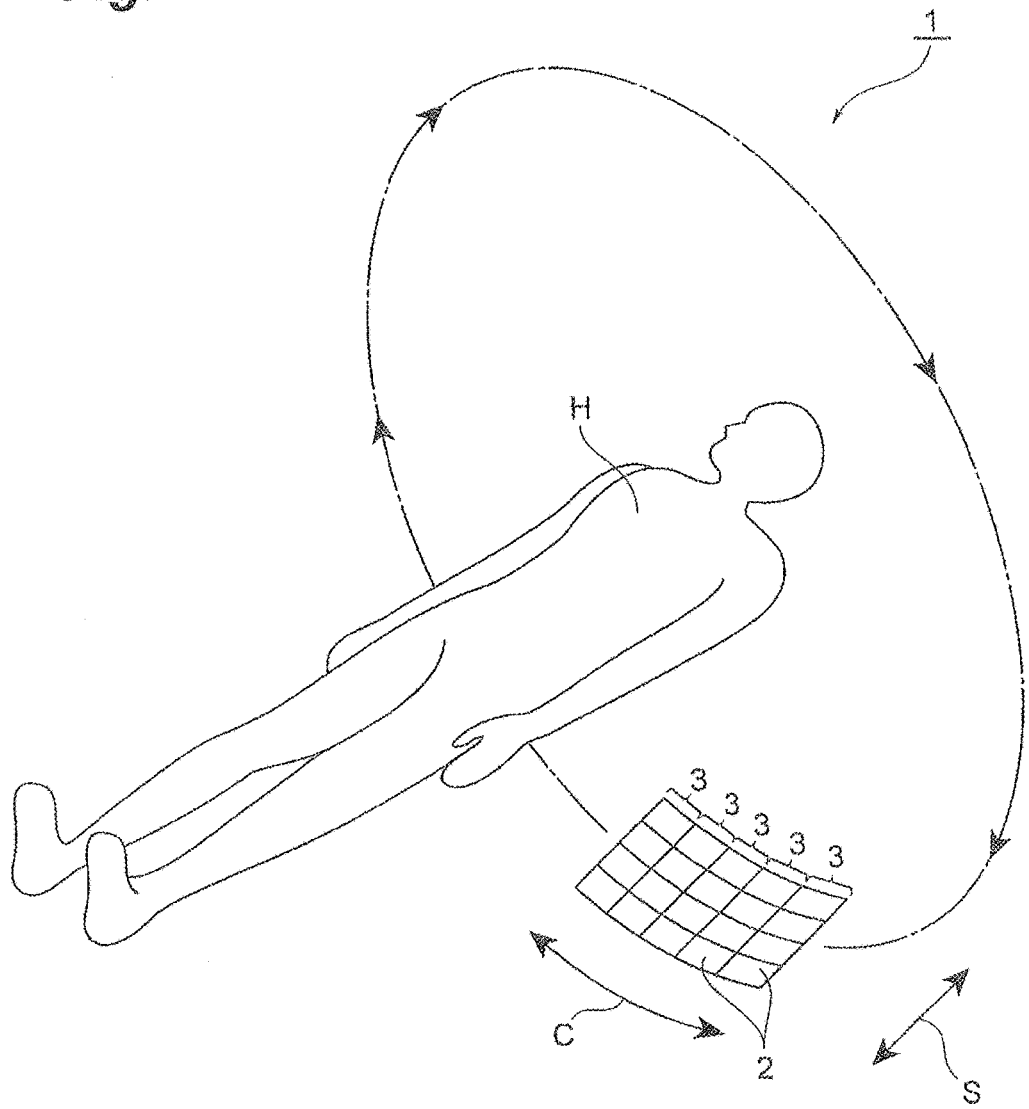
FIG. 1 is a schematic diagram illustrating a CT device equipped with a plurality of radiation detection units according to an embodiment.

FIG. 1 is a schematic diagram illustrating a CT device equipped with the plurality of radiation detection units according to an embodiment. As illustrated in FIG. 1, a CT device 1 irradiates radiation (X-ray, γ-ray, or the like) from a radiation source (not illustrated) to a subject H, and detects the radiation that has been transmitted through the subject H is detected by a plurality of detection modules (radiation detection module) 2. The plurality of detection modules 2 are fixed to a rotation mechanism (gantry) (not illustrated). The plurality of detection modules 2 rotates in a gantry rotating direction (channel direction) C and linearly moves in a slice direction (body axial direction) S.

The plurality of detection modules 2 is arranged in each of the channel direction C and the slice direction S. A detection unit (radiation detection unit) 3 is equipped with the plurality of detection modules 2 that is arranged in the slice direction S.

[Radiation Detection Unit]

Figure 2:
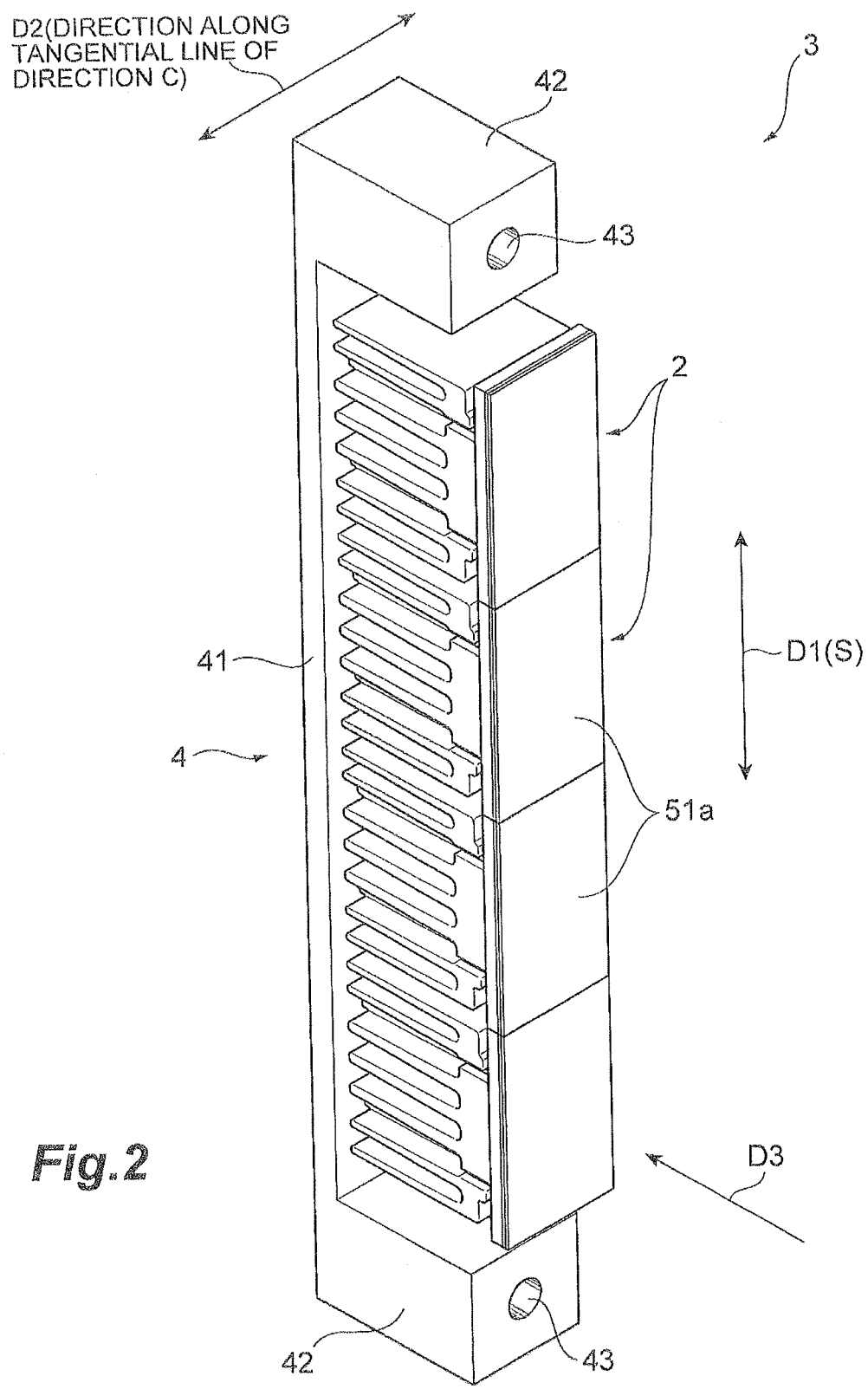
FIG. 2 is a perspective view of the radiation detection unit illustrated in FIG. 1.

FIG. 2 is a perspective view of the radiation detection unit illustrated in FIG. 1. Herein, the direction along the slice direction S is a first direction D1; the direction along a tangential line of the channel direction C (direction orthogonal to the first direction D1) is a second direction D2; and the direction along a normal of an incident surface 51a (described below) of the detection module 2 is a third direction D3.

As illustrated in FIG. 2, the detection unit 3 includes the plurality of above-described detection modules 2 and a frame 4. The frame 4 extends in the first direction D1. Specifically, the frame 4 includes a supporting portion 41 extending in the first direction D1, and in-frame abutment portions 42, 42 each of which is located on each of the end portions of the supporting portion 41 in the first direction D1.

The supporting portion 41 has a long plate-like shape. The in-frame abutment portion 42 has a rectangular parallelepiped shape and protrudes from one surface of the supporting portion 41. The in-frame abutment portion 42 has a through hole 43 for permitting penetration of a bolt B (refer to FIGS. 10 and 11; details will be described below). The plurality of detection modules 2 is mounted on the supporting portion 41 in the first direction D1. The detection module 2 is mounted spaced apart from one surface of the supporting portion 41 (refer to FIGS. 3 and 4; details will be described below).

[Radiation Detection Module]

Figure 3:
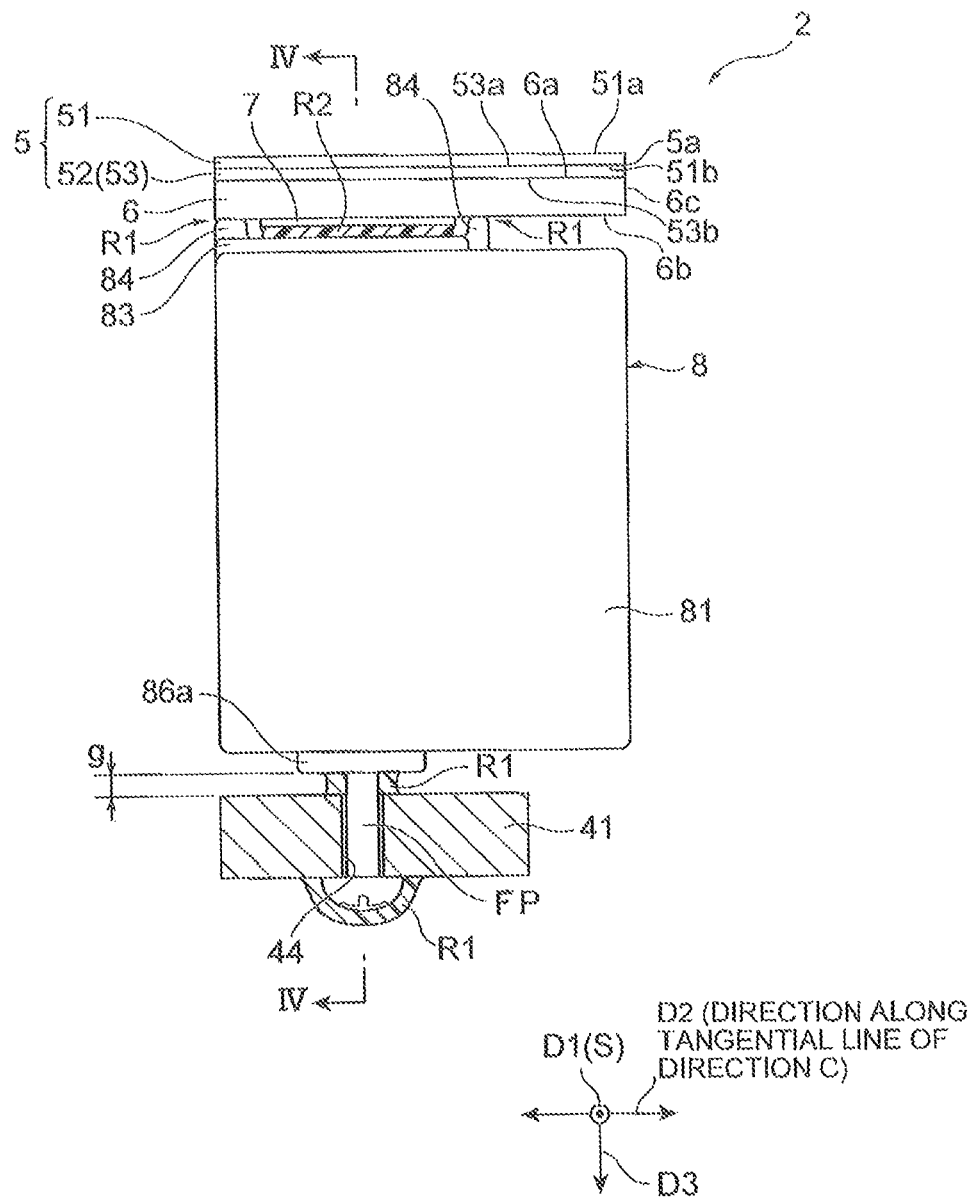
FIG. 3 is a side view of the radiation detection module illustrated in FIG. 2.
Figure 4:
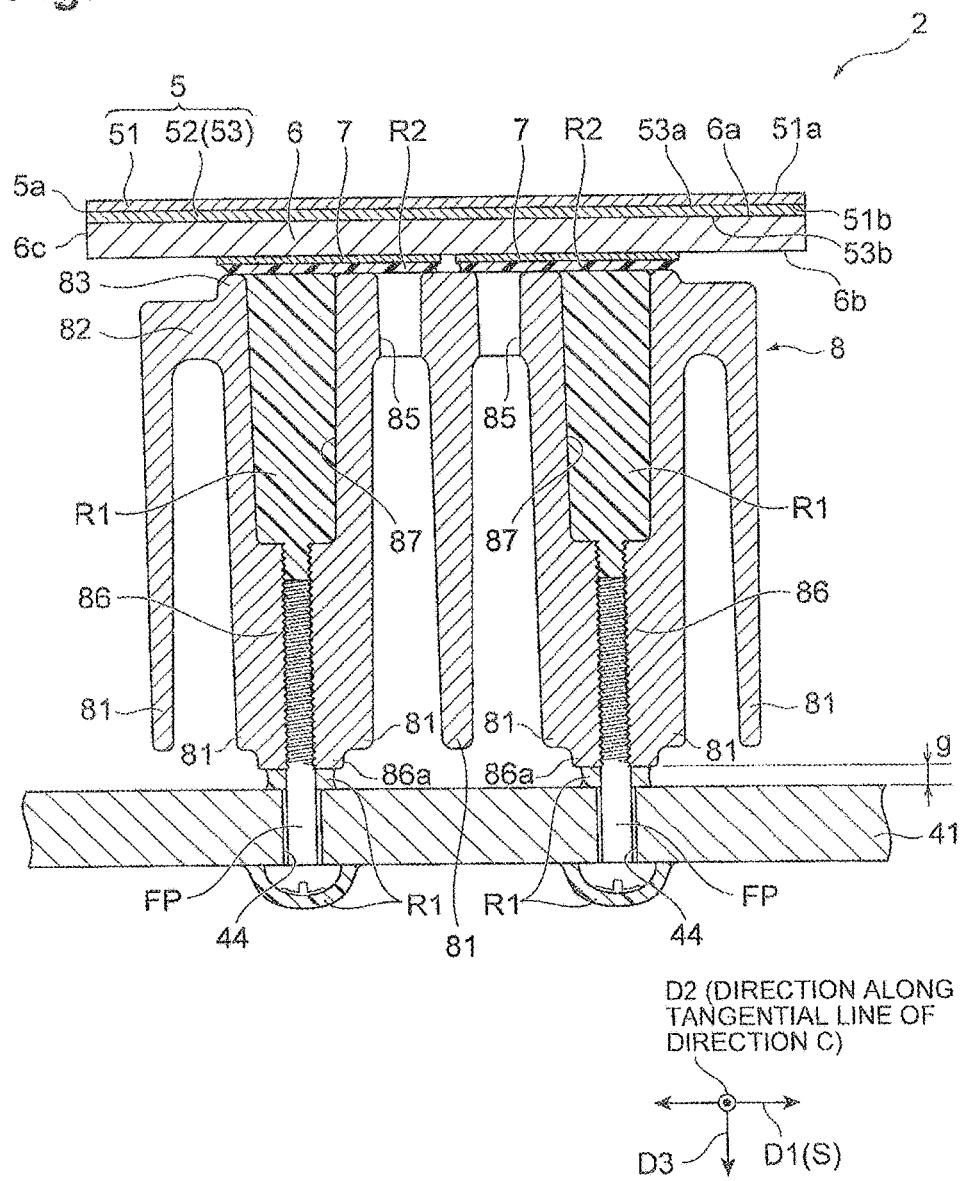
FIG. 4 is a diagram viewed in the arrow direction of the IV-IV line in FIG. 3.

FIG. 3 is a side view of the radiation detection module illustrated in FIG. 2. FIG. 4 is diagram viewed in the arrow direction of the IV-IV line in FIG. 3. As illustrated in FIGS.

3 and 4, the detection module 2 includes a detecting section 5, a supporting base plate 6, a processing section 7, and a heat radiating member 8.

The detecting section 5 includes a scintillator 51 and a photodiode array 52 (detecting element). The scintillator 51 has a rectangular (specifically, equiangular quadrilateral) plate shape (refer to FIG. 2). The scintillator 51 extends in the first direction D1 and the second direction D2. The scintillator 51 includes an incident surface 51a on which radiation is incident, and an emission surface 51b that is located on the opposite side of the incident surface 51a and emits scintillation light in response to incident radiation. Each of the incident surface 51a and the emission surface 51b extends in the first direction D1 and the second direction D2. The scintillator 51 is, for example, a CsI doped with Ti, or the like. The CsI has a structure including a forest of large number of needle-shaped crystals (columnar crystals).

The photodiode array 52 detects scintillation light from the scintillator 51. The photodiode array 52 includes a plurality of photodiodes (detecting elements) and a semiconductor substrate 53 that includes the plurality of photodiodes. The semiconductor substrate 53, when viewed in the third direction D3, has substantially the same shape as the scintillator 51, or the rectangular plate shape that is slightly larger than the scintillator 51. The semiconductor substrate 53 extends in the first direction D1 and the second direction D2. The plurality of photodiodes is arranged two-dimensionally on the semiconductor substrate 53. The semiconductor substrate 53 includes a first surface 53a on which scintillation light from the scintillator 51 is incident and a second surface 53b located on the opposite side of the first surface 53a. Each of the first surface 53a and the second surface 53b extends in the first surface D and the second direction D2. The scintillator 51 is located on the first surface 53a.

The semiconductor substrate 53 is formed of silicon or the like. The photodiode array 52 is, for example, a back-illuminated type in which, for example, a photosensitive region is located on the second surface 53b side. Note that the photodiode array 52 may be a front-illuminated type in which the photosensitive region thereof is located on the first surface 53a. When the photodiode array 52 is a front-illumination type, the photodiode and a land electrode (described below) of the supporting base plate 6 may be coupled via a through electrode formed inside the semiconductor substrate 53, or may be coupled by the wire bonding.

The photodiode array 52 is coupled to the emission surface 51b of the scintillator 51 via an optically transparent optical coupling agent with respect to the scintillation light from the scintillator 51. The photodiode array 52 has sensitivity, for example, ranging from an ultraviolet region to a near-infrared region. On the detecting section 5 as described above, a portion that is exposed in the first direction D1 and the second direction D2 that are orthogonal to the third direction (portion along the third direction D3) is a side portion 5a.

The supporting base plate 6 supports the detecting section 5 and the processing section 7. The supporting base plate 6 has substantially the same shape of a rectangular plate shape as the semiconductor substrate 53, when viewed in the third direction D3. The supporting base plate 6 extends in the first direction D1 and the second direction D2. The supporting base plate 6 has a first surface 6a that supports the detecting section 5, and a second surface 6b that is located on the opposite side of the first surface 6a and supports the processing section 7. Each of the first surface 6a and the second surface 6b extends in the first direction D1 and the second direction D2. On the supporting base plate 6, a portion exposed in the first direction D1 and the second direction D2 (portion along the third direction D3) is a side portion 6c. The supporting base plate 6 and the semiconductor substrate 53 are integrated.

On each of the first surface 6a and the second surface 6b of the supporting base plate 6, a land electrode is formed. On the land electrode of the first surface 6a, a photodiode of the semiconductor substrate 53 is coupled via a bump electrode. On the land electrode of the second surface 6b, the processing section 7 is coupled via a bump electrode. Inside the supporting base plate 6, a conductor pattern is formed for coupling the land electrodes of the first surface 6a and the second surface 6b to each other.

The supporting base plate 6, for example, is formed by laminating a plurality of green sheets containing ceramic and by firing the laminate structure. The supporting base plate 6 may be formed with an organic material (glass epoxy resin, or the like).

The processing section 7 processes a signal from the photodiode array 52. As illustrated in FIG. 4, the plurality of processing sections 7 is provided. The processing section 7, when viewed in the third direction D3, has a rectangular (specifically, equiangular quadrilateral) plate shape that is smaller than the supporting base plate 6. The plurality of processing sections 7, 7 is spaced apart from each other in the first direction D1. The processing section 7 is, for example, an application specific integrated circuit (ASIC).

Figure 5:
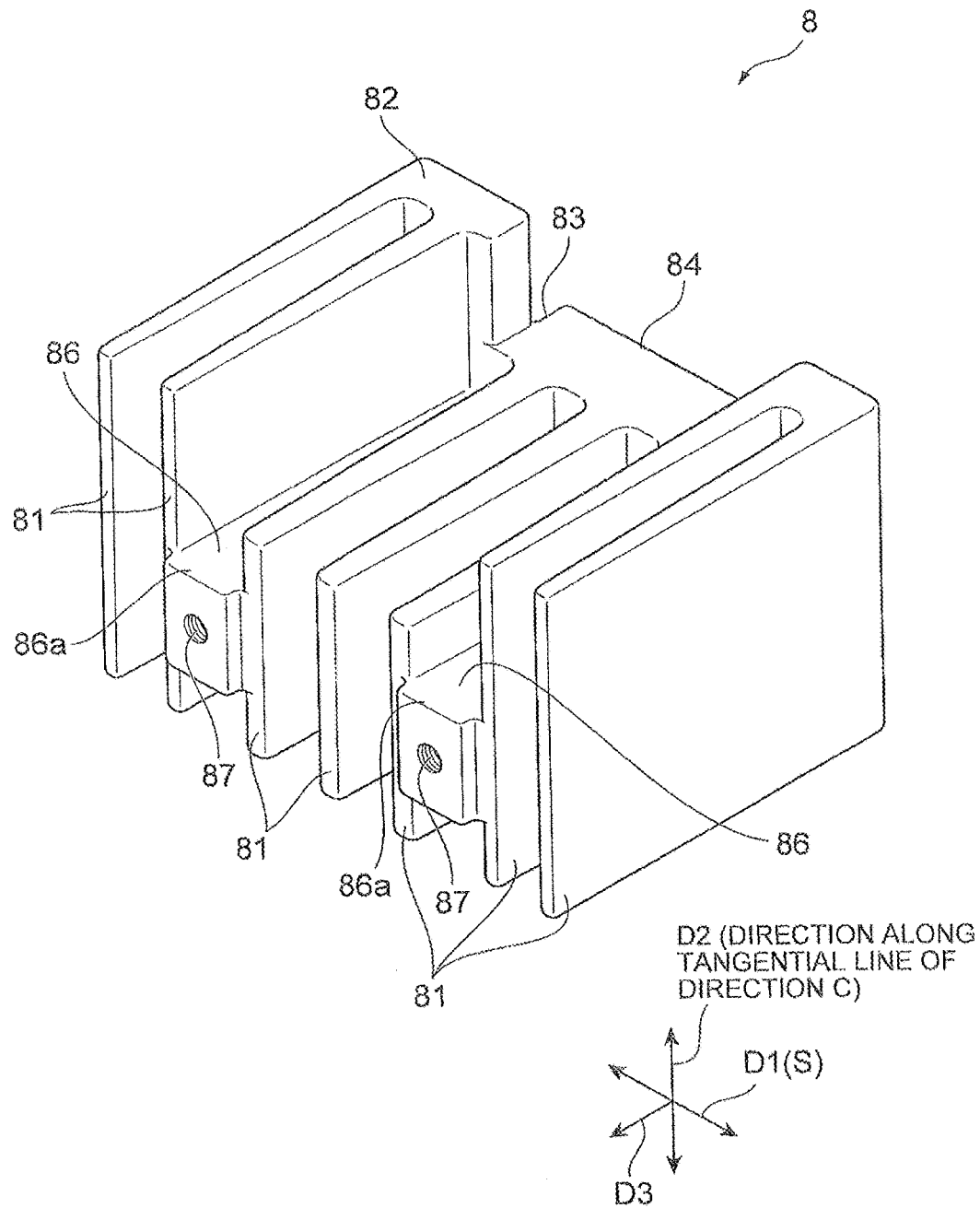
FIG. 5 is a perspective view of a heat radiating member illustrated in FIG. 4.

The heat radiating member 8 is thermally coupled to the processing sections 7, 7 and dissipates the heat generated by the processing sections 7, 7. FIG. 5 is a perspective view of the heat radiating member in FIG. 4. As illustrated in FIGS. 4 and 5, the heat radiating member 8 includes a plurality of fins 81. Specifically, the cross section of the heat radiating member 8 in the first and third directions D1 and D3 has a substantially comb-shape (see FIG. 4). A portion coupling a plurality of comb teeth is a base 82. Portions of the comb teeth are the above-described fins 81. The heat radiating member 8, when viewed in the third direction, is smaller than the supporting base plate 6 and is substantially U-shaped (refer to FIG. 5). Examples of a material for forming the heat radiating member 8 include Al, Cu, or brass.

The base 82 has a substantially plate shape. The base 82 extends in the first direction D1 and the second direction D2. The processing sections 7, 7 are thermally coupled at the base 82. Specifically, at the base 82, the center portion in the first direction D1 protrudes toward the processing section 7 side with respect to the both end portions. The protruding portion is a coupling portion 83 to which the processing sections 7, 7 are to be coupled. As illustrated in FIG. 3, a pair of fixed portions 84, 84 protrudes toward the supporting base plate 6 side from the coupling portion 83.

The fixed portion 84 has a substantially rectangular parallelepiped shape and extends in the first direction D1. The pair of fixed portions 84, 84 is spaced apart from each other in the second direction D2 and is located at both end portions of the coupling portion 83 in the second direction D2. The protrusion height of the fixed portion 84 is larger than the thickness of the processing section 7. The fixed portion 84 is fixed to the second surface 6b of the supporting base plate 6 by resin (first resin) R1. The resin R1, for example, may be an epoxy resin-based adhesive. The above-mentioned processing sections 7, 7 are arranged at a gap between the supporting base plate 6 and the coupling portion 83 formed by the fixed portions 84, 84.

As illustrated in FIG. 4, a plurality of through holes 85, 85 is provided at the coupling portion 83 corresponding to the number of processing sections 7. The through holes 85, 85 are spaced apart from each other in the first direction D1. The through hole 85 is provided between the pair of opposing fins 81, 81 in the first direction D1. The through hole 85 and the processing section 7 overlap with each other when viewed in the third direction D3.

Between the coupling portion 83 and the processing section 7, resin (second resin) R2 is sandwiched. For the resin R2, highly thermal conductive resin (for example, silicone resin) can be used. For example, highly thermally conductive resin having a higher thermal conductivity than that of the resin R1 can be used as the resin R2. The resin R2, for example, can be arranged in the following manner. First, the supporting base plate 6 and the fixed portion 84 are bonded with the resin R1. Subsequently, the resin R2 is inserted through the above-mentioned through holes 85, 85 into a space between the processing section 7 and the coupling portion 83.

The fin 81 protrudes toward the opposite side of the processing section 7 from the base portion 82 in the third direction D3. The Fin 81 has a plate shape extending so as to intersect the first direction D1. More specifically, the fin 81 has a plate shape extending so as to be substantially orthogonal to the first direction D1. In other words, the fin 81 has a plate shape extending in the second and third directions D2 and D3. In some gaps among the gaps between the pairs of opposing fins 81, 81, a coupling portion 86 that couples the pair of opposing fins 81, 81 is provided (see FIG. 5).

A plurality of (specifically, two) coupling portions 86 is provided in the first direction D1. The coupling portion 86 is provided at a gap that overlaps with the processing section 7 when viewed in the third direction D3. The coupling portions 86, 86 are arranged symmetrically with respect to a center of the detection module 2 in the first direction D1. The coupling portions 86, 86 are provided on the outer side, in the first direction D1, than the through holes 85, 85 into which the resin R2 is inserted as described above.

An end portion of the coupling portion 86 (lower end portion in FIGS. 3 and 4) protrudes more than an end portion of the fin 81. The end portion of the coupling portion 86 is located on the opposite side of the incident surface 51a on the detection module 2, and functions as a mounting portion 86a.

The coupling portion 86 has a through hole 87 in the third direction D3. The through hole 87 has a larger diameter at a portion on the base 82 side than the portion on the mounting portion 86a side. The through hole 87 has an internal thread that is formed at a portion on the mounting portion 86a side. On the detection module 2, a flexible flat cable (FFC) 9 is attached for outputting signals to the outside (refer to FIG. 7).

The above-described detection module 2 and the frame 4 are attached to each other via a rod-shaped supporting pin (rod member) FP. Specifically, a through hole 44 is provided on the supporting portion 41 of the frame 4 at a position corresponding to the through hole 87 of the heat radiating member 8. An external thread is formed on the supporting pin FP. The supporting pin FP is inserted through the through hole 44 of the supporting portion 41 and is screwed into the through hole 87 of the heat radiating member 8. A gap g exists between the supporting portion 41 and the coupling portion 86.

For fixing the detection module 2 and the frame 4, adhesive is used. As the adhesive, the above-described resin R1 may be used, for example. Specifically, the resin R1 is inserted in the through hole 87. A gap may be formed between the resin R1 and the resin R2. Between the end portion of the coupling portion 86 and the supporting portion 41, the resin R1 is attached so as to cover the supporting pin FP. In the supporting pin FP, a portion (head) protruding from the supporting portion 41 is covered with the resin R1.

[Jigs to be Used in Method for Producing Radiation Detection Unit]

Figure 6:
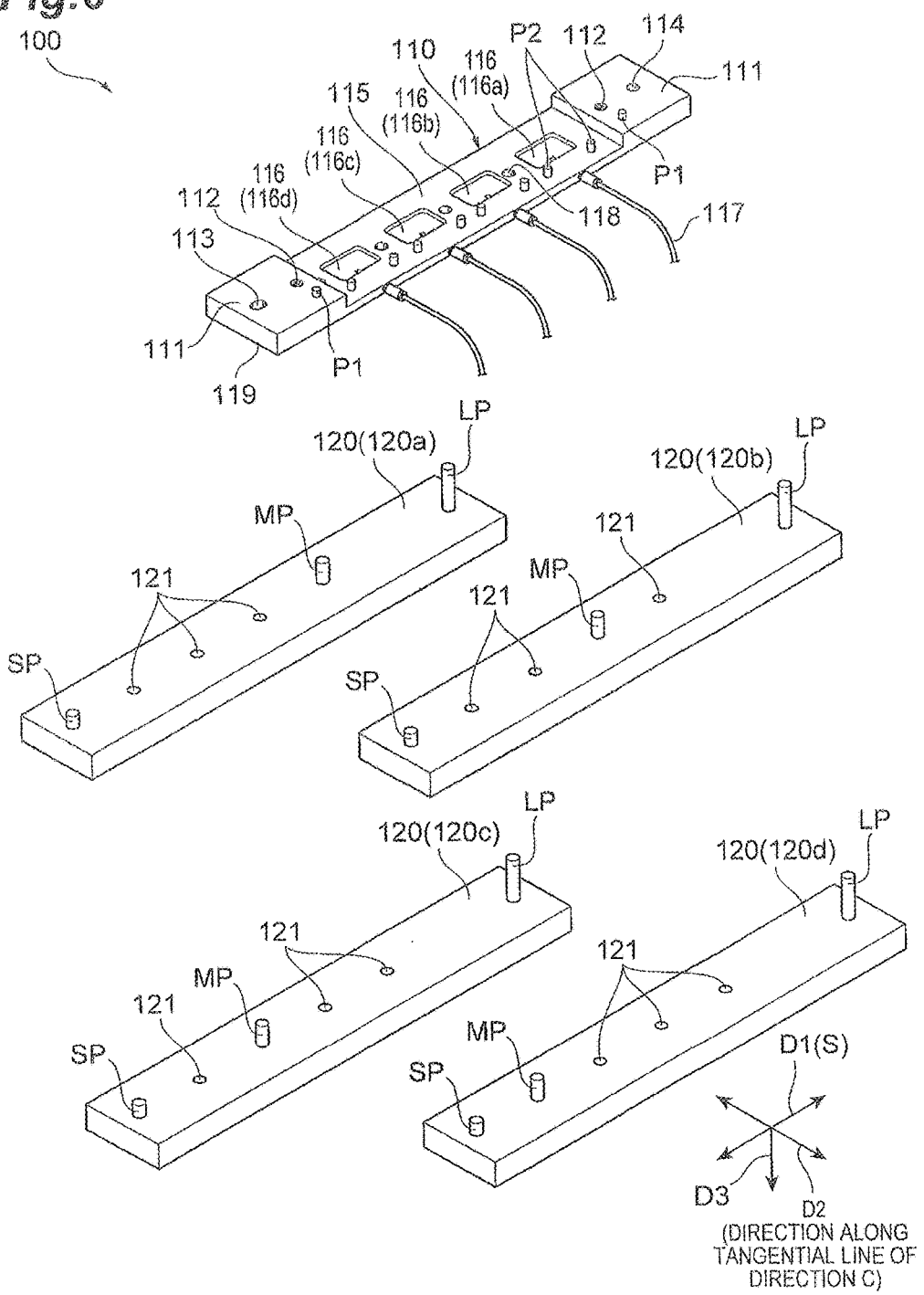
FIG. 6 is a perspective view of a jig to be used in a method for producing the radiation detection unit according to an embodiment.

FIG. 6 is a perspective view of a jig to be used in the method for producing the radiation detection unit according to an embodiment. A jig 100 includes a reference jig 110 and protrusion jigs 120. The plurality of protrusion jigs 120 is prepared corresponding to the number of detection modules 2 included in one detection unit 3.

The reference jig 110 has a substantially long plate shape longer than the above-described frame 4 (refer to FIGS. 10 and 11), and is used such that the longitudinal direction thereof is along the first direction D1. On one surface of the reference jig 110, the both end portions in the first direction D1 are in-jig abutment portions 111, 111, and a portion on the center is a reference surface 115.

The in-jig abutment portion 111 protrudes with respect to the reference surface 115. A protrusion height of the in-jig abutment portion 111 is predetermined so that, when the frame side abutment portion 42 of the above-described frame 4 and the in-jig abutment portion 111 are abutted, the distance between the supporting portion 41 of the frame 4 and the reference surface 115 of the reference jig 110 becomes greater than the height of the detection module 2 (length in the third direction D3) (refer to FIGS. 10 and 11).

The in-jig abutment portion 111 has a screw hole 112 for screwing the bolt B (refer to FIGS. 10 and 11) at a position corresponding to the above-described through hole 43 of the frame 4. The in-jig abutment portion 111 on one side (left hand-side in FIG. 6) has a long hole 113 for permitting penetration of a short pin SP (described below) at a position spaced apart from the screw hole 112 in the first direction D1. The long hole 113 extends in the first direction D1.

The in-jig abutment portion 111 on another side has a through hole 114 for permitting penetration of a long pin LP (described below) at a position spaced apart from the screw hole 112 in the first direction D1. On each of the in-jig abutment portions 111, 111, a pin P1 protrudes at a position spaced apart from the screw hole 112 in the second direction D2, the pin P1 being abutted by the frame 4 and positioning the frame 4. The pin P1 is fitted into a prepared hole.

On the reference surface 115, a plurality of chambers 116 is provided corresponding to the number of detection modules 2 included in one detection unit 3. The chamber 116 is recessed from the reference surface 115. The chamber 116, when viewed in the third direction D3, has a substantially rectangular (specifically, substantially equiangular quadrilateral) shape smaller than the above-described detecting section 5. The reference jig 110 has a flow path that communicates with each of the chambers 116. Piping 117 capable of sucking the air from the chamber 116 is connected to each of the flow paths.

In the reference surface 115, a through hole 118 for permitting penetration of a pin MP (described below) is located at a position spaced apart from each of the chambers 116 toward the long hole 113 (in-jig abutment portion 111 on one side) in the first direction D1. That is, the plurality of through holes 118 is provided corresponding to the number of detection modules 2 included in one detection unit 3. On the reference surface 115, a pair of pins P2, P2 protrudes at a position spaced apart from each of the chambers 116 in the second direction D2 and slightly outer position from each of the chambers 116 in the first direction D1, the pair of pins P2, P2 being abutted by the detection module 2 and positioning the detection module 2. The pin P2 is fitted into a prepared hole. On the reference jig 110, a surface on the opposite side of the reference surface 115 is a back surface 119.

Each of the protrusion jigs 120 has a long plate-like shape with substantially the same length as the reference jig 110, and is used such that the longitudinal direction thereof is along the first direction D1. On one surface of the protrusion jig 120, a short pin SP for positioning with respect to the reference jig 110 protrudes near the end portion on one side (left hand-side in FIG. 6) in the first direction D1. On one surface of the protrusion jig 120, a long pin LP for positioning with respect to the reference jig 110 protrudes near the end portion on another side. The long pin LP is longer than the short pin SP. Each of the long pins LP and short pins SP is fitted into a prepared hole.

On one surface of the protrusion jig 120, a plurality of pin holes 121 for fitting a pin MP is provided in the first direction D1 corresponding to the positions of the through holes 118 to 118 of the reference jig 110. The pin MP is longer than the short pin SP and shorter than the long pin LP.

Among the plurality of protrusion jigs 120, the protrusion jig 120 on which the pin MP is fitted into the pin hole 121 that is the first pin hole from the long pin LP side is a protrusion jig 120a. Among the plurality of protrusion jigs 120, the protrusion jig 120 on which the pin MP is fitted into the pin hole 121 that is the second pin hole from the long pin LP side is a protrusion jig 120b.

Among the plurality of protrusion jigs 120, the protrusion jig 120 on which the pin MP is fitted into the pin hole 121 that is the third pin hole from the long pin LP side is a protrusion jig 120c. Among the plurality of protrusion jigs 120, the protrusion jig 120 on which the pin MP is fitted into the pin hole 121 that is the fourth pin hole from the long pin LP side is a protrusion jig 120d.

[Method for Producing Radiation Detection Unit]

Figure 7:
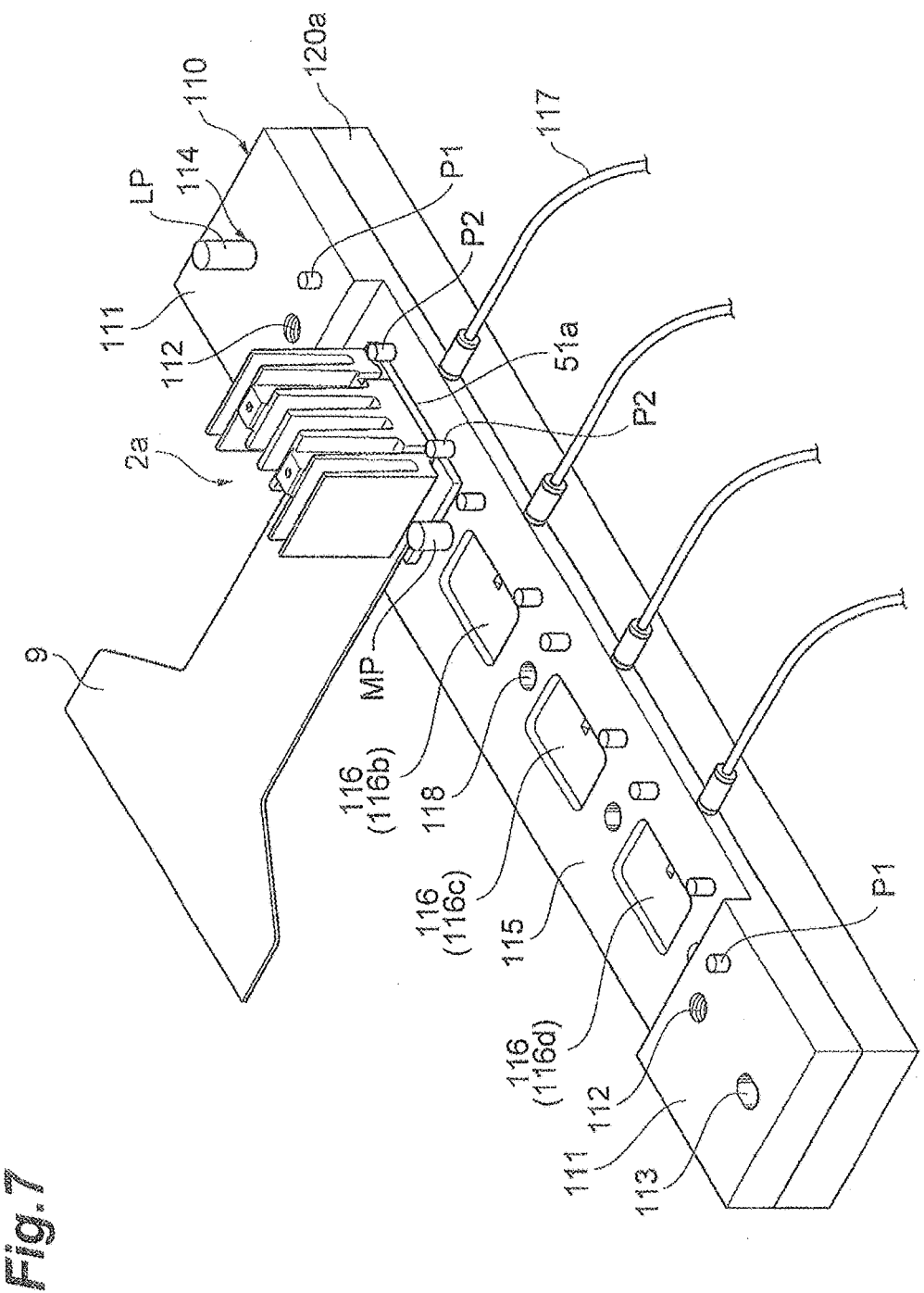
FIG. 7 is a perspective view of a step of the method for producing the radiation detection unit according to the embodiment.
Figure 8:
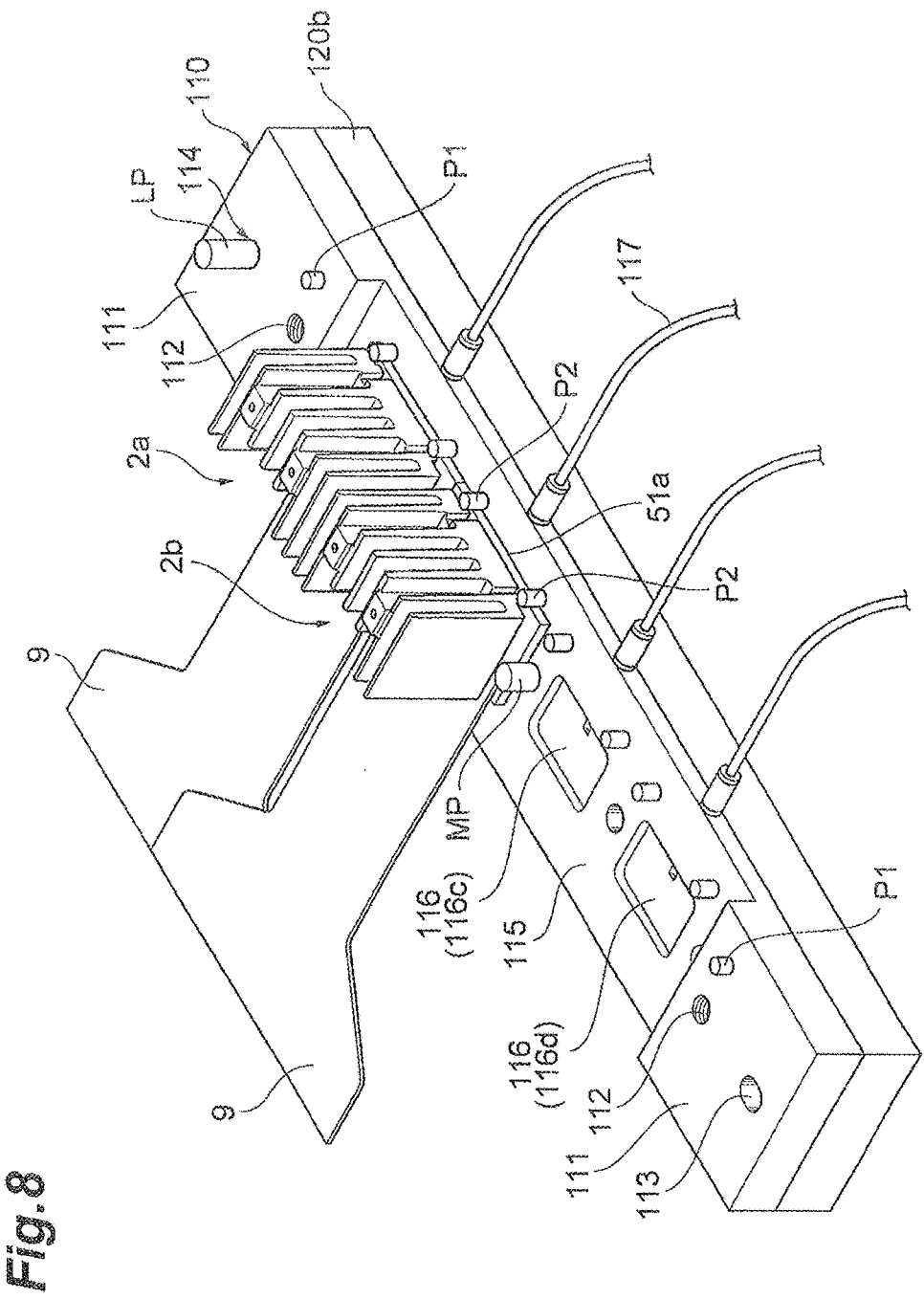
FIG. 8 is a perspective view of a step of the method for producing the radiation detection unit according to the embodiment.
Figure 9:
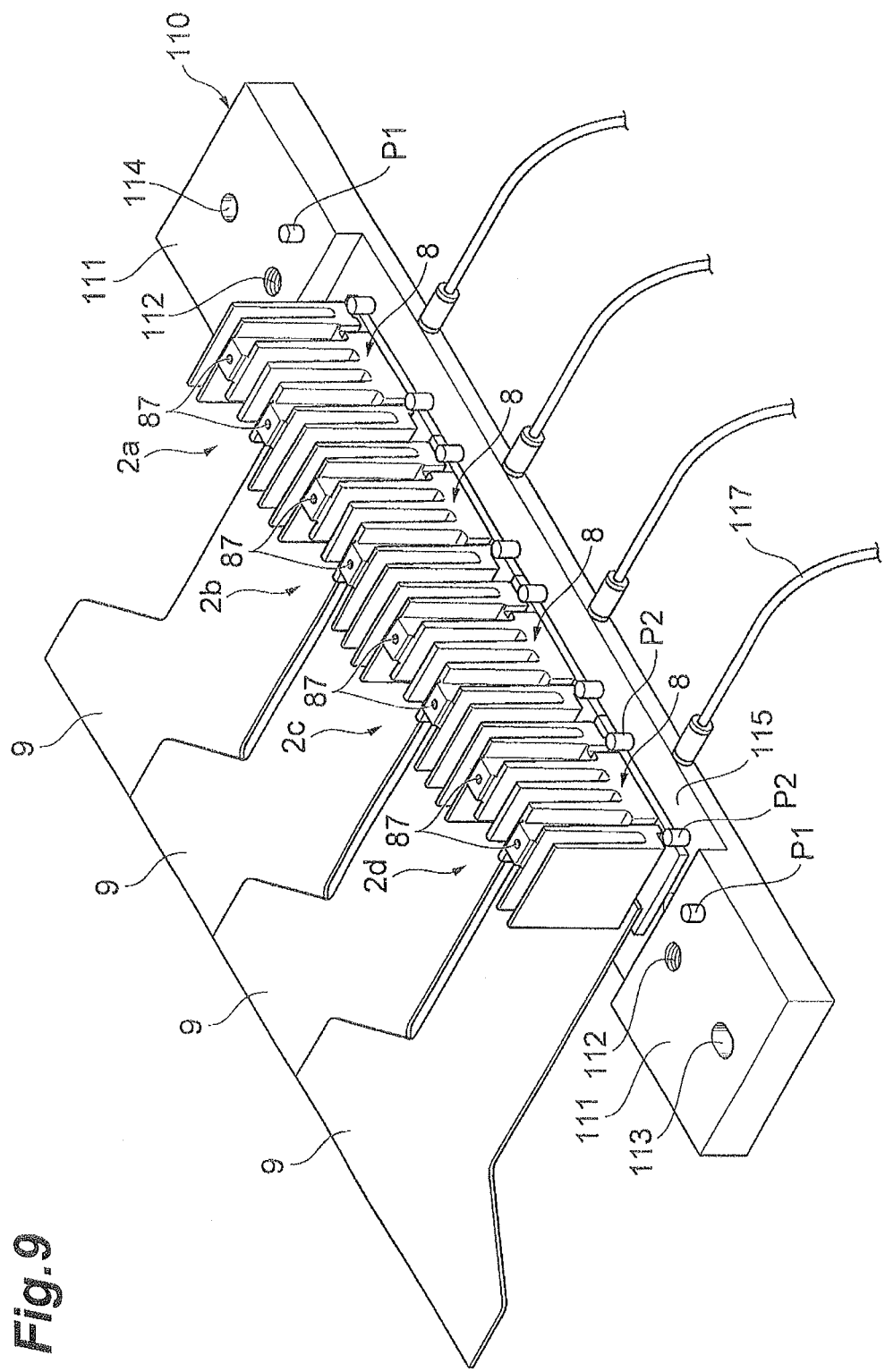
FIG. 9 is a perspective view of a step of the method for producing the radiation detection unit according to the embodiment.
Figure 10:
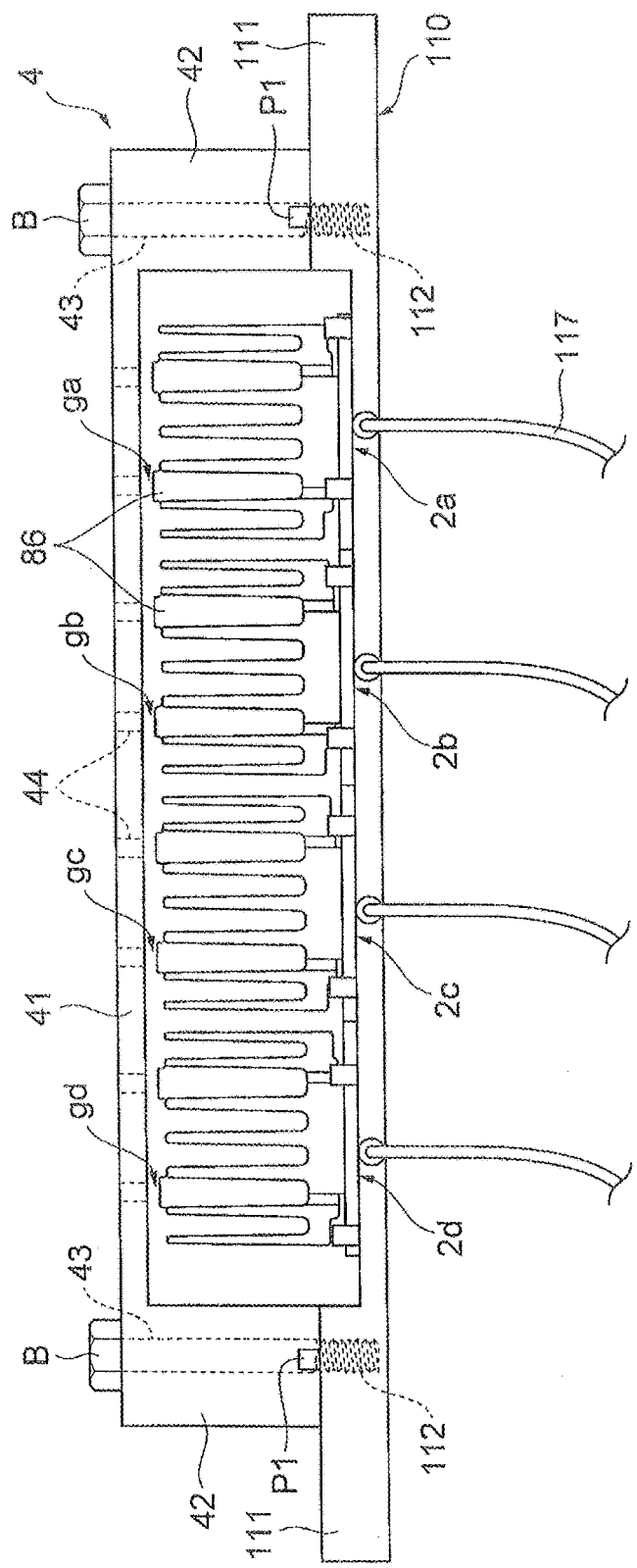
FIG. 10 is a front view of a step of the method for producing the radiation detection unit according to the embodiment.
Figure 11:
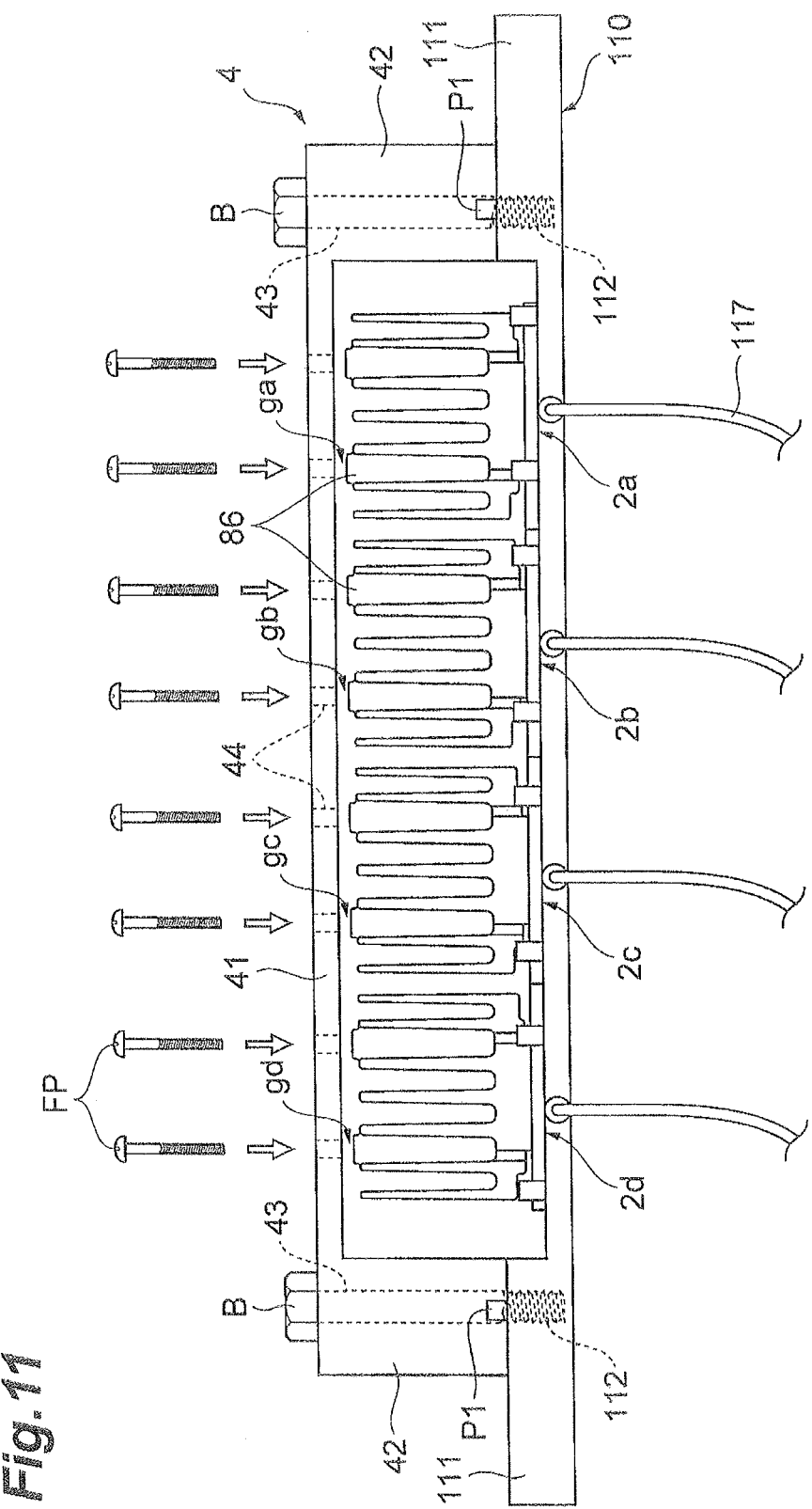
FIG. 11 is a front view of a step of the method for producing the radiation detection unit according to the embodiment.

FIGS. 7 to 9 are perspective views illustrating steps of the method for producing the radiation detection unit according to the embodiment. FIGS. 10 to 12 are front views illustrating steps of the method for producing the radiation detection unit according to the embodiment. The detection modules 2a to 2d have the same configuration as that of the above-described detection module 2.

According to the method for producing the detection unit 3 according to the present embodiment, as illustrated in FIG. 7, the reference jig 110 and the protrusion jig 120a (first protrusion jig) are used initially. The reference jig 110 and the protrusion jig 120a are combined so that the pin MP (first protrusion) penetrates the through hole 118 (first through hole) that is the first through hole from the through hole 114 (in-jig abutment portion 111 on the other side), from the back surface 119 to the reference surface 115, such that the pin MP protrudes from the reference surface 115 of the reference jig 110. At this time, the short pin SP is inserted through the long hole 113, and the long pin LP is inserted through the through hole 114.

Subsequently, the incident surface 51a of the detection module 2a (first radiation detection module) and the reference surface 115 are abutted so as to cover the chamber 116a that is the first chamber from the through hole 114. The side portion of the detection module 2a and the pin MP are abutted in the first direction D1. Furthermore, the side portion of the detection module 2a and the pins P2, P2 are abutted in the second direction D2. More specifically, the side portion 5a of the detecting section 5 and the side portion 6c of the supporting base plate 6 abut the pin MP or the pins P2, P2. Alternatively, the portion that has the largest protrusion among these portions abuts the pin MP or the pins P2, P2. Subsequently, internal air is sucked from the chamber 116a using the piping 117. In this manner, the detection module 2a is positioned (first step).

Subsequently, as illustrated in FIG. 8, the pin MP is removed from the reference surface 115 by removing the protrusion jig 120a from the reference jig 110. Subsequently, the reference jig 110 and the protrusion jig 120b (second protrusion jig) are used. The reference jig 110 and the protrusion jig 120b are combined so that the pin MP (second protrusion) penetrates the through hole 118 (second through hole) that is the second through hole from the through hole 114, from the back surface 119 to the reference surface 115, such that the pin MP protrudes from the reference surface 115 of the reference jig 110. At this time, the short pin SP is inserted through the long hole 113, and the long pin LP is inserted through the through hole 114.

Subsequently, the incident surface 51a of a detection module 2b (second radiation detection module) and the reference surface 115 are abutted so as to cover the chamber 116b that is the second chamber from the through hole 114. At this time, the detection module 2b is arranged within a region from which the pin MP (first protrusion) used at positioning of the above-described detection module 2a has been removed. In other words, the detection module 2b is arranged such that the first through hole 118 from the through hole 114 from which the pin MP (first protrusion) has been removed is covered with the incident surface 51a. In this manner, the detection modules 2a and 2b are arranged close to each other.

The side portion of the detection module 2b and the pin MP are abutted in the first direction D1. Furthermore, the side portion of the detection module 2b and the pins P2, P2 are abutted in the second direction D2. More specifically, the side portion 5a of the detecting section 5 and the side portion 6c of the supporting base plate 6 abut the pin MP or the pins P2, P2. Alternatively, the portion that has the largest protrusion among these portions abuts the pin MP or the pins P2, P2. Subsequently, internal air is sucked from the chamber 116b using the piping 117. In this manner, the detection module 2b is positioned (second step).

Subsequently, as illustrated in FIG. 9, the above-described steps are repeated; the detection module 2c is positioned using the reference jig 110 and the protrusion jig 120c; the detection module 2d is positioned using the reference jig 110 and the protrusion jig 120d. Subsequently, the resin R1 is inserted into each of the through holes 87 on each of the heat radiating members 8.

Subsequently, as illustrated in FIG. 10, each of the in-jig abutment portions 111, 111 of the reference jig 110 and each of the in-frame abutment portions 42, 42 of the above-described frame 4 are abutted. In this manner, on each of the detection modules 2a to 2d, the mounting portion 86a of the heat radiating member 8 is arranged opposing the supporting portion 41 of the frame 4 while spaced apart from the supporting portion 41.

The side portion of the in-frame abutment portion 42 and the pin P1 are abutted. The bolt B is inserted through the through hole 43 of the in-frame abutment portion 42, and screwed into the screw hole 112 of the in-jig abutment portion 111 so as to fasten the reference jig 110 and the frame 4.

At this time, gaps ga to gd exist between the supporting portion 41 and the mounting portion 86a of the detection modules 2a to 2d, respectively. On the detection modules 2a to 2d, in a case where a dimensional error and an assembly error of each of components exit in the third direction D3, the sizes of the gaps ga to gd vary since the incident surface 51a of the detection modules 2a to 2d abuts the reference surface 115 that is common to the modules. That is, the dimensional error and the assembly error of each of the components on the detection modules 2a to 2d are absorbed at the gaps ga to gd.

Subsequently, as illustrated in FIG. 11, the supporting pin FP is inserted through each of the through holes 44 of the frame 4, and screwed into each of the through holes 87 of the detection modules 2a to 2d (refer to FIG. 5). At this time, the supporting pin FP is screwed into the through hole 87 such that each of the incident surfaces 51a of the detection module 2a to 2d may not be separated from the reference surface 115.

Subsequently, as illustrated in FIG. 12, on each of the detection modules 2a to 2d, the resin R1 is applied to a space between the mounting portion 86a and the supporting portion 41 so as to cover the supporting pin FP. The head of each of the supporting pins FP is covered with the resin R1. In this manner, each of the detection modules 2a to 2d is fixed to the frame 4 (third step). Subsequently, suction of the chambers 116a to 116d is released, and the reference jig 110 is removed from the frame 4. The detection unit 3 is produced in the above steps.

As described above, in the method for producing the detection unit 3 according to the present embodiment, each of the detection modules 2a to 2d is positioned in each of separate steps. This enables suppressing accumulation of the dimensional error and the assembly error of the detection modules 2a to 2d. Accordingly, this improves positional accuracy of the detection modules in the arrangement direction of the detection modules 2a to 2d.

In the method for producing the detection unit 3, the pin MP for positioning the detection modules 2a to 2d can be removed from the jig 100. When the detection modules 2b to 2d that are positioned secondly or later are being positioned, the detection modules 2b to 2d are arranged in a region from which the pin MP has been removed. This enables arranging the detection modules 2a to 2d close to each other. Accordingly, this reduces the distance between the adjacent detection modules.

In the method for producing the detection unit 3, the mounting portion 86a of the detection modules 2a to 2d is attached to the frame 4 at a spaced position in a state on which the incident surface 51a of the detection modules 2a to 2d abuts the reference surface 115 that is common surface to the modules. This makes it possible to align the incident surfaces 51a of the detection modules 2a to 2d, and simultaneously absorb the dimensional error and the assembly error of the detection modules 2a to 2d, at the gaps ga to gd. Accordingly, this improves positional accuracy of the detection module in a normal direction of the incident surface 51a.

On each of the mounting portions 86a of the detection modules 2a to 2d, the through hole 87 into which the supporting pin FP can be inserted is provided. The resin R1 is filled and the supporting pin FP is inserted to each of the through holes 87 so as to attach each of the detection modules 2a to 2d to the frame 4 via each of the supporting pins FP. The method enables fixing each of the detection modules 2a to 2d to the frame 4 firmly and with high accuracy with adhesive (resin R1).

The jig 100 includes the reference jig 110 and the protrusion jigs 120a to 120d. The reference jig 110 includes the reference surface 115 and the back surface 119 that is the opposite side of the reference surface 115. Each of the protrusion jigs 120a to 120d has the pin MP. The reference jig 110 includes the through holes 118 to 118 through which the pin MP penetrates from the back surface 119 to the reference surface 115. In positioning the detection module 2a, the reference jig 110 and the protrusion jig 120a are combined for use such that the pin MP protrudes from reference surface 115. In positioning the detection module 2b, the reference jig 110 and the protrusion jig 120b are combined for use such that the pin MP protrudes from the reference surface 115 after the protrusion jig 120a has been removed from the reference jig 110. With this method, it is only required that the protrusion jig 120a is removed from the back surface 119 side of the reference jig 110 when the pin MP is removed from the jig 100. This facilitates removing the ping MP from the jig 100. Accordingly, this improves assemblability of the detection unit 3.

The frame 4 extends in the first direction D1 along the slice direction S of the CT device 1. The detection modules 2a to 2d are mounted on the frame 4 in the first direction D1. The method makes it possible to improve positional accuracy of the detection module in the slice direction S.

The method for producing the radiation detection unit according to the embodiment has been described as above. The present invention, however, is not limited to the above-described embodiment. For example, according to the above-described embodiment, the reference jig 110 and the protrusion jigs 120a to 120d are used as the jig 100. Alternatively, the reference jig 110 alone can be used as in the following. First, the reference jig 110 is prepared on which the pin MP is directly fitted into each of the through holes 118 to 118.

Subsequently, the incident surface 51a of the detection module 2a and the reference surface 115 are abutted so as to cover the chamber 116a that is the first chamber from the through hole 114. The side portion of the detection module 2a and the pin MP are abutted in the first direction D1. Furthermore, the side portion of the detection module 2a and the pins P2, P2 are abutted in the second direction D2. More specifically, the side portion 5a of the detecting section 5 and the side portion 6c of the supporting base plate 6 abut the pin MP or the pins P2, P2. Alternatively, the portion that has the largest protrusion among these side portions abuts the pin MP or the pins P2, P2. Subsequently, internal air is sucked from the chamber 116a using the piping 117. In this manner, the detection module 2a is positioned (first step).

Subsequently, the pin MP that is the first pin from the through hole 114 is removed from the reference jig 110. Subsequently, the incident surface 51a of the detection module 2b and the reference surface 115 are abutted so as to cover the chamber 116b that is the second chamber from the through hole 114. At this time, the detection module 2b is arranged within a region from which the pin MP used at positioning of the above-described detection module 2a has been removed. In other words, the detection module 2b is arranged such that the through hole 118 that is the first through hole from the through hole 114 and from which the pin MP has been removed is covered with the incident surface 51a.

The side portion of the detection module 2b and the pin MP are abutted in the first direction D1. Furthermore, the side portion of the detection module 2b and the pins P2, P2 are abutted in the second direction D2. More specifically, the side portion 5a of the detecting section 5 and the side portion 6c of the supporting base plate 6 abut the pin MP or the pins P2, P2. Alternatively, the portion that has the largest protrusion among these side portions abuts the pin MP or the pins P2, P2. Subsequently, internal air is sucked from the chamber 116b using the piping 117. In this manner, the detection module 2b is positioned (second step).

Subsequently, the above-described steps are repeated to position the detection modules 2c and 2d. The subsequent steps are the same as in the above-described embodiment. To sum up, the first radiation detection module and the second radiation detection module are positioned sequentially by using a jig from which the first protrusion used for positioning the first radiation detection module is removable. In positioning the second radiation detection module, the second radiation detection module is arranged in a region from which the first protrusion has been removed.

According to the above-described embodiment, the detecting section 5 includes the scintillator 51 and the photodiode array 52. Alternatively, the detecting section 5 may be a direct detection type detecting element (element that uses a crystal such as CdTe, CdZnTe) that directly detects radiation. Configuration, the numbers, and the material of each of the components are not limited to the configuration, the numbers, and the material in the above-described embodiment, but may be modified appropriately.

INDUSTRIAL APPLICABILITY

The present invention is applicable to the production of a radiation detection unit for a CT device.

REFERENCE SIGNS LIST

1 CT device
2 detection module (first radiation detection module, second radiation detection module)
2a detection module (first radiation detection module)
2b, 2c detection module (first radiation detection module, second radiation detection module)
2d (second radiation detection module)
3 detection unit (radiation detection unit)
4 frame
51a incident surface
86a mounting portion
87 through hole (hole into which a rod member can be inserted)
100 jig
110 reference jig
115 reference surface
118 through hole (first through hole, second through hole)
119 back surface
120a protrusion jig (first protrusion jig)
120b, 120c protrusion jig (first protrusion jig, second protrusion jig)
120d protrusion jig (second protrusion jig)
FP supporting pin (rod member)
MP pin (first protrusion, second protrusion)
S slice direction
D1 first direction

The invention claimed is:
1. A method for producing a radiation detection unit for a CT device, the radiation detection unit comprising
a first radiation detection module and a second radiation detection module, each module configured to detect radiation, and
a frame configured to support each of the first radiation detection module and the second radiation detection module,
wherein each of the first radiation detection module and the second radiation detection module includes an incident surface on which radiation is incident, a mounting portion located on an opposite side of the incident surface, and a side portion exposed in a direction orthogonal to a normal of the incident surface,
the method for producing the radiation detection unit being implemented by using a jig including a reference surface, a first protrusion protruding from the reference surface, and a second protrusion protruding from the reference surface, the first protrusion being removable from the jig,
the method for producing the radiation detection unit comprising:
a first step of abutting the incident surface of the first radiation detection module and the reference surface of the jig so as to position the first radiation detection module;
a second step of abutting the incident surface of the second radiation detection module and the reference surface of the jig so as to position the second radiation detection module; and
a third step of mounting each of the first radiation detection module and the second radiation detection module on the frame,
wherein, in the first step, the side portion of the first radiation detection module and the first protrusion are abutted,
in the second step, the second radiation detection module is arranged within a region from which the first protrusion has been removed and the side portion of the second radiation detection module and the second protrusion are abutted, after the first step, and
in the third step, each of the mounting portion of the first radiation detection module and the mounting portion of the second radiation detection module is arranged opposing the frame while spaced apart from the frame and each of the first radiation detection module and the second radiation detection module is mounted on the frame.

2. The method for producing the radiation detection unit according to claim 1,
wherein a hole into which a rod member can be inserted is provided on each of the mounting portion of the first radiation detection module and the mounting portion of the second radiation detection module, and
in the third step, adhesive is filled in each of the hole of the first radiation detection module and the hole of the second radiation detection module, the rod member is inserted into each of the holes, and each of the first radiation detection module and the second radiation detection module is mounted on the frame via the rod member.

3. The method for producing the radiation detection unit according to claim 1,
wherein the jig includes a reference jig having the reference surface and a back surface on the opposite side of the reference surface, a first protrusion jig having the first protrusion, and a second protrusion jig having the second protrusion,
the reference jig includes a first through hole for the first protrusion to penetrate from the back surface to the reference surface, and a second through hole for the second protrusion to penetrate from the back surface to the reference surface, in the first step, the reference jig and the first protrusion jig are combined for use such that the first protrusion protrudes from the reference surface, and in the second step, after the first protrusion jig has been removed from the reference jig, the reference jig and the second protrusion jig are combined for use such that the second protrusion protrudes from the reference surface.

4. The method for producing the radiation detection unit according to claim 1, wherein the frame extends in a first direction along a slice direction of the CT device, and the first radiation detection module and the second radiation detection module are mounted on the frame along the first direction.

\* \* \* \* \*